(12) United States Patent
Jeon et al.

(10) Patent No.: US 10,961,176 B2
(45) Date of Patent: Mar. 30, 2021

(54) **COMPOUND HEXADECAPHLORETHOL ISOLATED FROM *ISHIGE OKAMURAE* AND USE THEREOF**

(71) Applicant: Jeju National University Industry-Academic Cooperation Foundation, Jeju-do (KR)

(72) Inventors: You-Jin Jeon, Jeju-do (KR); BoMi Ryu, Jeju-do (KR)

(73) Assignee: Jeju National University Industry-Academic Cooperation Foundation, Jeju-do (KR)

( * ) Notice: Subject to any disclaimer, the term of this patent is extended or adjusted under 35 U.S.C. 154(b) by 0 days.

(21) Appl. No.: 16/749,030

(22) Filed: Jan. 22, 2020

(65) Prior Publication Data

US 2020/0157031 A1 May 21, 2020

Related U.S. Application Data

(63) Continuation of application No. 16/192,216, filed on Nov. 15, 2018, now abandoned.

(30) Foreign Application Priority Data

| Jun. 4, 2018 | (KR) | 10-2018-0063998 |
| Jun. 4, 2018 | (KR) | 10-2018-0063999 |
| Jun. 4, 2018 | (KR) | 10-2018-0064000 |

(51) Int. Cl.

| *A61K 31/09* | (2006.01) |
| *A61K 36/03* | (2006.01) |
| *A23L 33/10* | (2016.01) |
| *A61P 21/00* | (2006.01) |
| *C07C 43/295* | (2006.01) |

(52) U.S. Cl.
CPC ............ *C07C 43/295* (2013.01); *A23L 33/10* (2016.08); *A61K 36/03* (2013.01); *A23V 2002/00* (2013.01)

(58) Field of Classification Search
CPC ......... A61K 31/09; A61K 36/03; A23L 33/10; A61P 21/00; A23V 2002/00; A23V 2200/316; A23V 2250/202
See application file for complete search history.

(56) References Cited

PUBLICATIONS

Ryu et al., Ishophloroglucin A, a Novel Phlorotannin for Standardizing the Anti-α-Glucosidase Activity of Ishige okamurae, Marine Drugs, vol. 16, pp. 436-446 (Year: 2018).*

Lee, SH, et al. (2012) "Octaphlorethol A, a novel phenolic compound isolated from a brown alga, *Ishige foliacea*, increases glucose transporter 4-mediated glucose uptake in skeletal muscle cells.", *Biochemical and Biophysical Research Communications*, 420:576-581.

Office Action (Non-Final) from corresponding U.S. Appl. No. 16/192,216, dated Aug. 15, 2019.

Office Action (Final) from corresponding U.S. Appl. No. 16/192,216, dated Oct. 24, 2019.

* cited by examiner

*Primary Examiner* — Brenda L Coleman
(74) *Attorney, Agent, or Firm* — Harness, Dickey & Pierce. P.L.C.

(57) ABSTRACT

Disclosed herein are hexadecaphlorethol (HdP), which is a novel compound isolated from *Ishige okamurae*, and the use thereof in anti-diabetic treatment and exercise performance improvement. The novel compound HdP has the activity of inhibiting α-glucosidase, inducing glucose uptake into differentiated myoblast C2C12 cells, reducing blood glucose levels in zebrafish which have reduced insulin secretion through treatment with alloxan, increasing an intracellular level of calcium ions necessary for muscle contraction and exercise performance in zebrafish, and inducing uptake of glucose, an energy source necessary for muscle contraction, into cells.

8 Claims, 10 Drawing Sheets

Table 1. $^1$H, $^{13}$C and HMQC Data of HPP*

| No | $\delta_H$ (mult, J) | $\delta_C$ (mult) | No | $\delta_H$ (mult, J) | $\delta_C$ (mult) | No | $\delta_H$ (mult, J) | $\delta_C$ (mult) | No | $\delta_H$ (mult, J) | $\delta_C$ (mult) |
|---|---|---|---|---|---|---|---|---|---|---|---|
| 1 | | 156.2(s) | 26 | 5.85(1H,s) | 94.7(d) | 51 | 5.85(1H,s) | 94.7(d) | 76 | | 154.0(s) |
| 2 | 5.95(1H,d,J=1.6Hz) | 94.2(d) | 27 | | 151.1(s) | 52 | | 154.0(s) | 77 | 5.85(1H,s) | 94.7(d) |
| 3 | | 151.1(s) | 28 | | 122.0(s) | 53 | 5.85(1H,s) | 94.7(d) | 78 | | 151.1(s) |
| 4 | | 122.0(s) | 29 | | 151.1(s) | 54 | | 151.1(s) | 79 | | 152.7(s) |
| 5 | | 151.1(s) | 30 | 5.85(1H,s) | 94.7(d) | 55 | | 123.4(s) | 80 | | 123.5(s) |
| 6 | 5.95(1H,d,J=1.6Hz) | 94.2(d) | 31 | | 154.1(s) | 56 | | 150.8(s) | 81 | | 150.8(s) |
| 7 | | 154.0(s) | 32 | 5.85(1H,s) | 94.7(d) | 57 | 5.60(1H,d, J=1.6Hz) | 94.1(d) | 82 | 5.70(1H,d,J=1.8Hz) | 94.9(d) |
| 8 | 5.85(1H,s) | 94.7(d) | 33 | | 151.1(s) | 58 | | 153.0(s) | 83 | | 152.9(s) |
| 9 | | 151.1(s) | 34 | | 122.8(s) | 59 | 5.75(1H,dd, J=1.8,1.6Hz) | 94.7(d) | 84 | 5.75(1H,dd,J=1.8,1.6Hz) | 94.7(d) |
| 10 | | 122.8(s) | 35 | | 151.1(s) | 60 | | 152.7(s) | 85 | | 122.0(s) |
| 11 | | 151.1(s) | 36 | 5.85(1H,s) | 94.7(d) | 61 | | 123.4(s) | 86 | | 151.1(s) |
| 12 | 5.85(1H,s) | 94.7(d) | 37 | | 154.1(s) | 62 | | 152.7(s) | 87 | 5.85(1H,s) | 94.7(d) |
| 13 | | 154.1(s) | 38 | 5.85(1H,s) | 94.7(d) | 63 | 5.75(1H,dd, J=1.8,1.6Hz) | 94.7(d) | 88 | | 154.5(s) |
| 14 | 5.85(1H,s) | 94.7(d) | 39 | | 151.1(s) | 64 | | 153.0(s) | 89 | 5.85(1H,s) | 94.7(d) |
| 15 | | 151.1(s) | 40 | | 122.0(s) | 65 | 5.60(1H,d, J=1.6Hz) | 94.1(d) | 90 | | 151.1(s) |
| 16 | | 122.8(s) | 41 | | 151.1(s) | 66 | | 150.8(s) | 91 | | 161.0(s) |
| 17 | | 151.1(s) | 42 | 5.85(1H,s) | 122.0(s) | 67 | | 123.4(s) | 92 | 6.15(2H,d, J=1.6Hz) | 94.9(d) |
| 18 | 5.85(1H,s) | 94.7(d) | 43 | | 152.9(s) | 68 | | 150.8(s) | 93 | | 158.6(s) |
| 19 | | 154.1(s) | 44 | | 123.5(s) | 69 | 5.60(1H,d, J=1.6Hz) | 94.1(d) | 94 | 5.95(1H,d,J=1.6Hz) | 94.1(d) |
| 20 | 5.85(1H,s) | 94.7(d) | 45 | | 150.8(s) | 70 | | 153.0(s) | 95 | | 158.6(s) |
| 21 | | 151.1(s) | 46 | 5.70(1H,d, J=1.8Hz) | 94.9(d) | 71 | 5.75(1H,dd, J=1.8,1.6Hz) | 94.7(d) | 96 | 6.15(2H,d, J=1.6Hz) | 94.9(d) |
| 22 | | 122.0(s) | 47 | | 152.9(s) | 72 | | 152.7(s) | -OH* | 8.92-9.07 (33H,m) | |
| 23 | | 151.1(s) | 48 | 5.75(1H,dd, J=1.8,1.6Hz) | 94.7(d) | 73 | | 122.0(s) | | | |
| 24 | 5.85(1H,s) | 94.7(d) | 49 | | 122.0(s) | 74 | | 151.1(s) | | | |
| 25 | | 154.1(s) | 50 | | 151.1(s) | 75 | 5.85(1H,s) | 94.7(d) | | | |

*Recorded in DMSO-$d_6$ at 400 MHz for $^1$H NMR and 100 MHz for $^{13}$C NMR; -OH*: all free phenol hydroxyl groups

FIG. 3

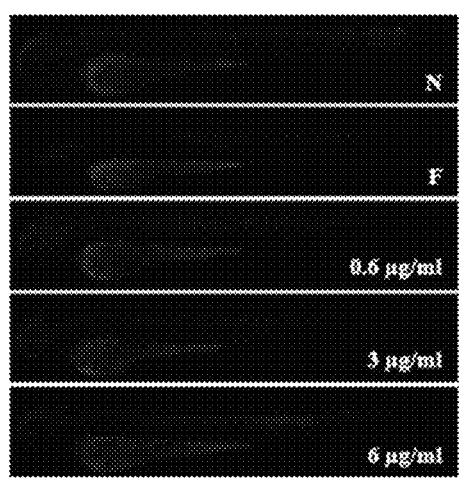
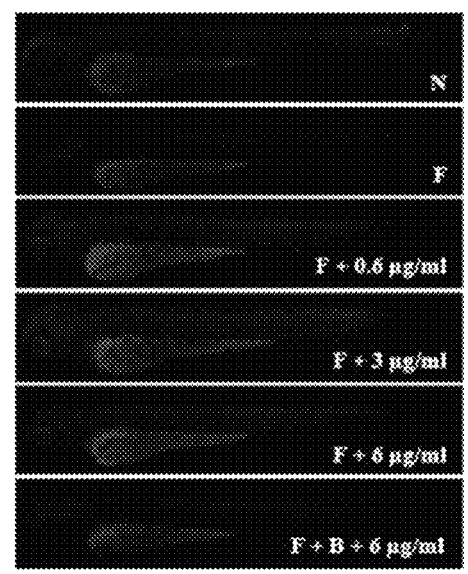
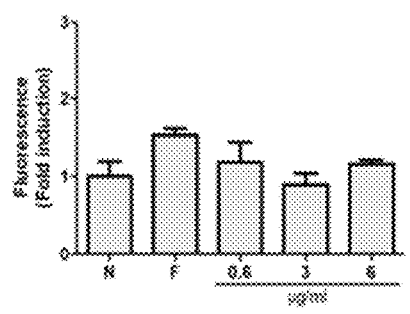
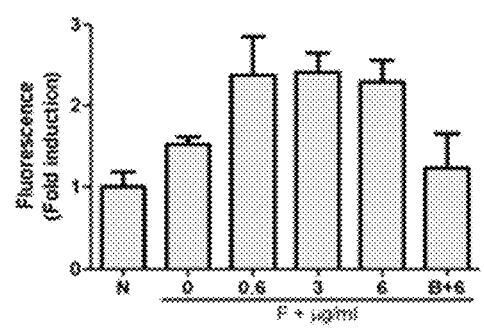
FIG. 9

COMPOUND HEXADECAPHLORETHOL ISOLATED FROM *ISHIGE OKAMURAE* AND USE THEREOF

CROSS-REFERENCE TO RELATED APPLICATIONS

This application is a continuation application of U.S. application Ser. No. 16/192,216, filed on 15 Nov. 2018, which claims priority to Korean Patent Application Nos. 10-2018-0063998, filed on 4 Jun. 2018, 10-2018-0063999, filed on 4 Jun. 2018 and 10-2018-0064000, filed on 4 Jun. 2018. The entire disclosures of the applications identified in this paragraph are incorporated herein by reference.

FIELD

The present disclosure relates to hexadecaphlorethol, which is a novel compound isolated from *Ishige okamurae*, and use thereof and, more particularly, to hexadecaphlorethol and the use thereof in anti-diabetes treatment and exercise performance improvement.

BACKGROUND

Diabetes mellitus, commonly referred to as diabetes, is generally classified into insulin-dependent diabetes (type I diabetes) and non-insulin-dependent diabetes (type II diabetes). Insulin-dependent diabetes is characterized by insulin deficiency resulting from the loss of the insulin-producing beta cells of the pancreatic islets, caused by, for example, viral infection. Non-insulin-independent diabetes is traditionally termed "juvenile diabetes" because a majority of these diabetes cases occur in young people in their teens or twenties. As known by the name itself, insulin-dependent diabetes implies the requirement of external insulin supply for life maintenance. Non-insulin-independent diabetes begins with insulin resistance, a condition in which cells fail to respond to insulin properly, which is mainly caused by obesity. As the disease progresses, insulin, although secreted from the beta cells of the pancreas, may become deficient. Non-insulin-dependent diabetes is mostly found in people in their thirties or later and is referred to as adult-onset diabetes. The name non-insulin-dependent diabetes implies that external insulin supply is not indispensable for life maintenance, but does not mean that insulin is unnecessary for regulating high blood sugar.

Diabetes is accompanied by complications including myocardial infarction, angina pectoris, damage to the eye, foot ulcers, etc. as chronic high blood sugar lasts with deficient insulin action. Insulin regulates the metabolism of carbohydrates, fats, and proteins by promoting the absorption of glucose from blood into liver, fat, and skeletal muscle cells. Diabetes is fundamentally an aberrant carbohydrate metabolism which results, however, in aberrance in protein and protein metabolism and electrolyte metabolism in vivo. In this context, diabetes is a group of metabolic disorders (J Korean Soc Food Sci Nutr. 2002 31:1071-1077). Therefore, the regulation of blood sugar is believed to be a therapy for preventing or delaying the onset of acute complications attributed to diabetes.

Carbohydrates in the digestive organs are degraded by α-amylase and α-glucosidase and other digestive enzymes finally into glucose and fructose which are then absorbed into villi of the small intestine. In a patient with diabetes who cannot effectively regulate blood sugar, glucose is not properly processed, thus aggravating the hyperglycemic state. Inhibition of α-amylase and α-glucosidase in the digestive organs makes the uptake of glucose slow, thereby regulating post-meal blood sugar (Int J Obes. 1984. 8 Suppl 1:181-90; Asia Pac J Clin Nutr. 2004. 13 (4):401-8; J Int Med Res. 1998 Oct.-Nov. 26 (5):219-32; Diabetes Care. 1999 Jun. 22 (6):960-4).

Particularly, α-glucosidase is an enzyme that acts at the final step of carbohydrate digestion to catalyze conversion into glucose. An α-glucosidase inhibitor can aid to regulate blood sugar by interfering with the degradation of polysaccharides into monosaccharides to delay sugar uptake (Journal of Life Science. 2008. 18 (7):1005-1010; J. Ethnopharmacol. 2000. 72:129-133). According to the mechanism thereof, an α-glucosidase inhibitor interferes with sugar uptake in the small intestine without acting on the secretion of insulin, thereby minimizing side-effects of conventional drugs, such as hypoglycemia, hepatotoxicity, beta cell hypofunction, etc. (European Journal of Pharmacology. 2009. 615:252-256; Journal of Life Science. 2008. 18 (7):1005-1010; Food Chem. 2008. 108:965-972).

Widely used as α-glucosidase inhibitors in clinics are acarbose and voglibose. Particularly, acarbose is known to have a useful anti-diabetic effect by suppressing glucose uptake in the small intestine (Eur J Clin Invest. 1994 August, 24 Suppl 3:3-10), but may produce gastroenteric troubles such as abdominal distension, abdominal pain, vomiting, diarrhea, etc. as well as side effects, such as gas, diarrhea, and constipation, caused by the degradation of undigested disaccharides by bacteria in the large intestine (World J Gastroenterol. 2008 Oct. 21. 14 (39):6087-92). In contrast, complete inhibition of α-glucosidase remarkably reduces glucose uptake, causing hypoglycemia and the use of α-glucosidase initiators is thus followed by problems (Mol Cell Biochem. 1998 May, 182 (1-2):101-8). Therefore, there is still continuation of a need for the development of a novel α-glucosidase that can reduce such side effects and exert the effect of suppressing post-meal blood sugar elevation.

Skeletal muscle has the principal role of relaxing and contracting muscles. In this regard, calcium ions in the cytoplasm of skeletal muscle cells act as a core secondary transmitter in the contraction and relaxation of skeletal muscle. Calcium ions play an important extra- and intracellular role in the human body and are minutely controlled to maintain proper functions thereof in various tissues. Extracellular calcium is involved in the excitation-contraction coupling of the heart and muscle and in the synaptic transmission of the nerve system as well as being a main component of the cartilage and bone. Intracellular calcium is maintained at a concentration 10,000-fold lower than that of extracellular calcium, playing a key role as a signal transmitter in cell division, muscular contraction, cell migration, membrane transmission, and secretion (Clin J Am Soc Nephrol. 2010. 5 Suppl 1:S23-30; Nephro Physiol. 2011. 118:22-7; Nat. Rev. Mol. Cell. Biol. 2003.4:517-29).

The concentration of intracellular free calcium ions is much lower than that of extracellular fluid upon stability, but the depolarization of a myocyte membrane in response to nerve stimulation causes the influx or release of calcium ions into the cytoplasm from extracellular fluid or an intracellular calcium reservoir. When the intracellular calcium concentration reaches a certain level, muscle contraction occurs. Particularly, skeletal muscle contraction persists even upon removal of calcium outside myocytes. Hence, muscles are known as an important intracellular calcium reservoir (Annul. Rev. Physiol. 1976. 38:293-313; Physio. Rev. 1977. 71-108).

Also, an elevated intracellular calcium level is known to induce mitochondrial respiration and ATP production (Am J Physiol Cell Physiol. 2004. 287:817-833; Biochemistry. 2013. 52:2793-2809). When muscles are given a stimulus, SR (sarcoplasmic reticulum) Ca2+ pumps (SERCA, a calcium pump present on the surface of the sarcoplasmic reticulum moves calcium ions from the cytosol of the cell to the lumen of the SR to control the homeostasis of intracellular calcium ion concentrations) act to transfer calcium ions to the SR to form actin-myosin bonds, resulting in muscle contraction. After muscle contraction, calcium ions return back to the original position (extracellular space through SR) by active transport at an expense of ATP which binds to myosin to cleave the actin-myosin bond, allowing muscle relaxation.

The ATP necessary for the active transport is generated through three metabolic energy pathways including the phosphagen system, glycolysis, and the aerobic system. Particularly, an increase in glucagon release is most important for producing needed glucose during exercise (J Clin Invest. 1984. 74 (4):1404-13). It is reported that exercise increases the number of glucose transporter type 4 (GLUT4) expressed in cell membranes and the concentration of GLUT4 in cell tissues (JAMA. 1991. 266:1535-42; J Clin invest. 1979. 64:1011-15; Am J Physiol. 1987. 252:E170-175), which supports the opinion that an increase in the glucose uptake of muscles during exercise promotes the regeneration of ATP, increasing the rate of glucose transport.

In addition, glycogen depletion in the muscle and the liver during exercise is a main cause of fatigue and ATP in skeletal muscles is an immediately usable energy source generated in mitochondria upon muscular contraction. Therefore, a glycogen content in skeletal muscles or an ATP content in muscles, measured by using cell experiments or liver or muscle tissues of experimental animals, is used as a biomarker in the functionality evaluation for exercise performance capacity (Guideline of functionality evaluation for health functional food, 2016, the Korean Ministry of Food and Drug Safety).

The present disclosure discloses the novel material HdP isolated and identified from *Ishige okamurae* and its anti-diabetic activity and activity of enhancing exercise performance.

SUMMARY

A purpose of the present disclosure is to provide a composition for improving exercise performance, using HdP, a novel material isolated and identified from *Ishige okamurae*.

Other or concrete purposes of the present disclosure will be proposed, below.

BRIEF DESCRIPTION OF THE DRAWINGS

The above and other objects, features and advantages of the present invention will be more clearly understood from the following detailed description taken in conjunction with the accompanying drawings, in which:

FIG. 3 is 1H and 13C NMR spectral data of HdP;
FIG. 9 shows a result illustrating that HdP increases an intracellular calcium ion (Ca2+) level in zebrafishes.

DESCRIPTION OF THE PREFERRED EMBODIMENTS

Figure 1:
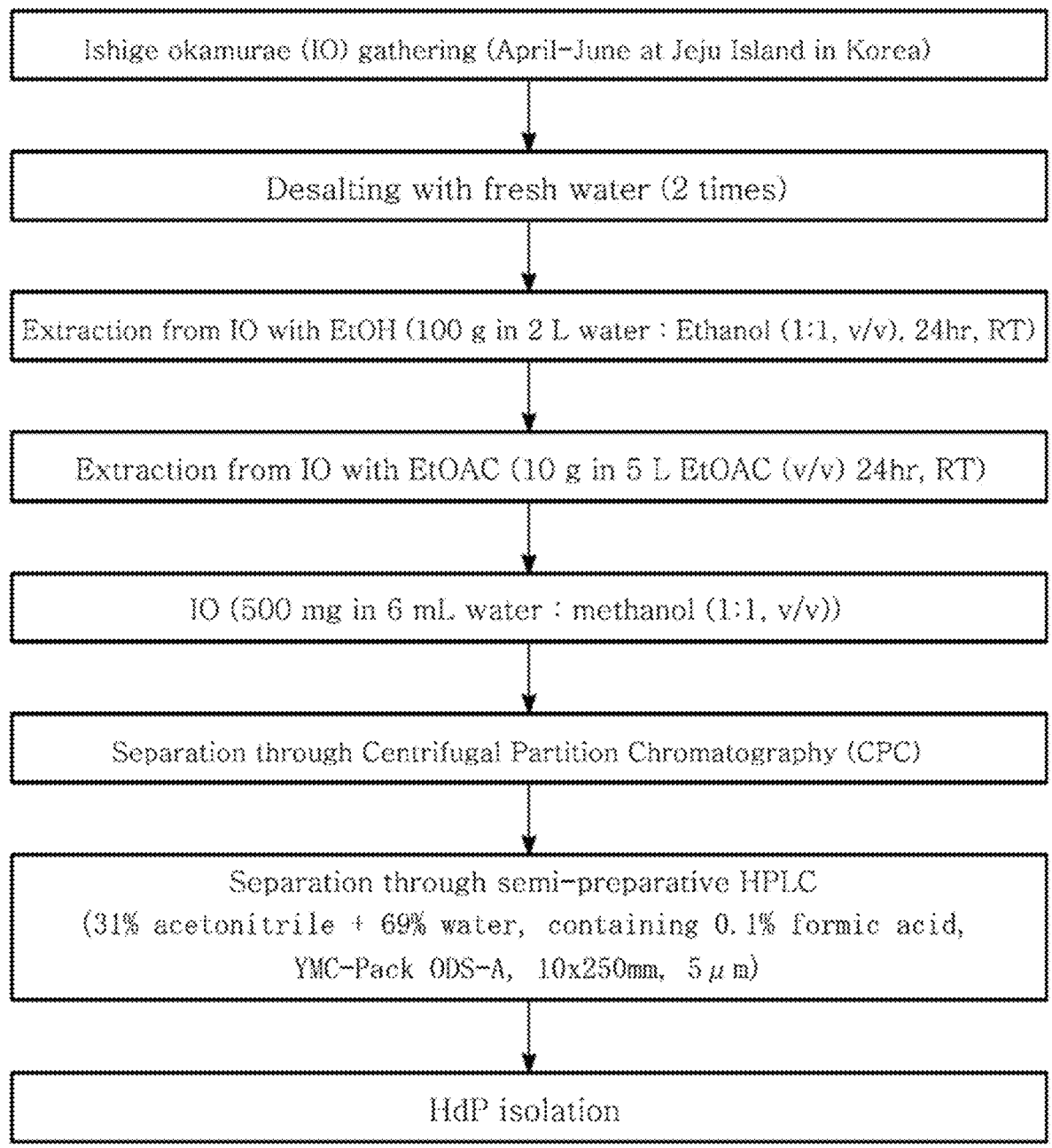
FIG. 1 schematically illustrate an HdP isolation process.

As illustrated in the following Examples and Experimental Examples, the novel material HdP of the following Chemical Formula 1, isolated and identified from *Ishige okamurae*, was found to inhibit the activity of α-glucosidase and to induce glucose uptake in C2C12, which is a differentiated myoblast cell line. As shown in zebrafish experiments, the novel material was observed to reduce blood glucose levels in zebrafish which was rendered to secrete a reduced level of insulin by treatment with alloxan, increase an intracellular concentration of calcium ions necessary for muscle contraction and motility enhancement, and induce intracellular uptake of glucose, which is an energy source necessary for muscle contraction.

<Chemical Formula 1>

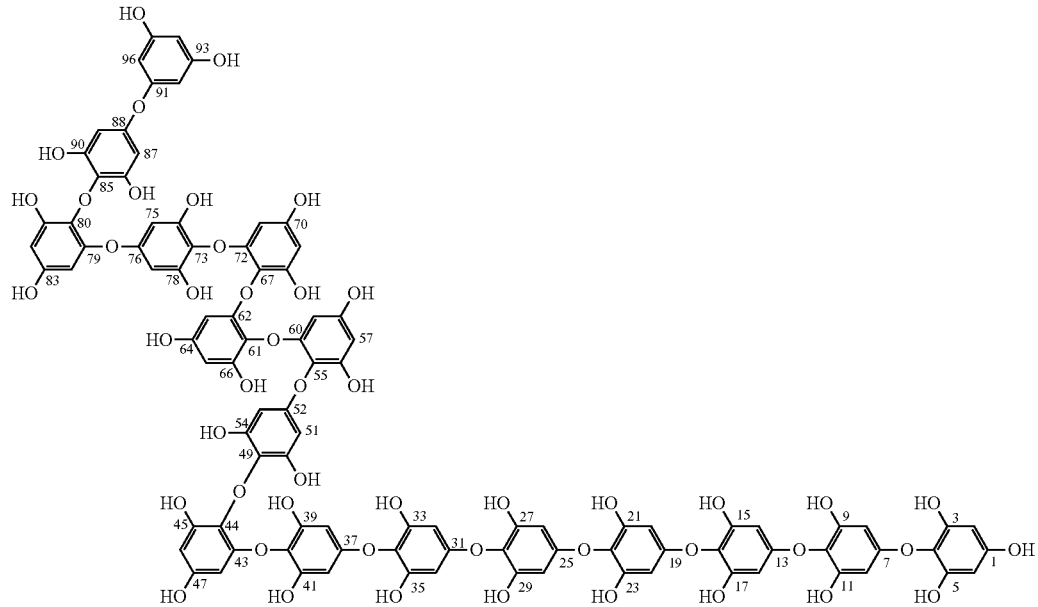

With the above-mentioned experimental results taken into consideration, one aspect of the present disclosure contemplates the compound represented by Chemical Formula 1, a prodrug thereof, a hydrate thereof, or a solvate thereof. Another aspect of the present disclosure contemplates an anti-diabetic composition comprising the compound of Chemical Formula 1, a prodrug thereof, a hydrate thereof, or a solvate thereof as an effective ingredient. A further aspect of the present disclosure contemplates a composition comprising the compound of Chemical Formula 1, a prodrug thereof, a hydrate thereof, or a solvate thereof as an effective ingredient for improving exercise performance.

As used herein, the term "prodrug" refers to a drug that has a physically or chemically controlled property by chemically modifying a target drug and is itself biologically inactive, but is converted to a bioactive drug by chemical or enzymatic action in vivo after administration.

As used herein, "hydrate" means a compound that is associated with water, without chemical bonds between water and the compound.

As used herein, "solvate" means a compound formed between molecules or ions of a solute and molecules or ions of a solvent.

The term "anti-diabetic" or "anti-diabetes", as used herein, means alleviation, prevention, or treatment of a symptom of diabetes.

The term "diabetes", as used herein, means insulin-dependent diabetes mellitus (type 1 diabetes mellitus) and non-insulin dependent diabetes mellitus (type 2 diabetes mellitus) and is further intended to encompass diabetes resulting from pancreatic damage caused by a different disorder, for example, diabetes caused by hyperthyroidism, hyperadrenocorticism, hypersecretion of growth hormone, or hypersecretion of catecholamine, and gestational diabetes.

The term "effective ingredient", as used herein, means an ingredient that can exhibit a desired activity by itself or in combination with a carrier which is itself not active.

So long as the effective ingredient exhibits an effect of improving exercise performance, a certain amount (effective amount) thereof may be contained in the composition of the present disclosure and may vary, depending on use, formulation, etc. Typically, the effective ingredient may be determined within the range of 0.001% by weight to 15% by weight. Here, the term "effective amount" refers to an amount of an effective ingredient contained in the composition of the present disclosure which is capable of producing a desirable medical and pharmaceutical effect such as exercise performance improvement, etc., when the composition is administered to a subject, such as a mammal, particularly a human, for a period of administration according to the suggestion of a medical expert. Such an effective amount may be empirically determined within the typical ability of a person skilled in the art.

In addition to the effective ingredient, the composition of the present disclosure may further comprise any compound or natural extract that has been verified for safety and known to have corresponding activities in order to synergistically reinforce an anti-diabetic effect or an exercise performance improvement effect or to increase the convenience of administration or intake through addition of similar activities such as body fat reduction, fatigue alleviation, etc.

Such compounds or extracts may be compounds or extracts described in the official compendium of each country, such as pharmacopoeia (e.g., Korean Pharmacopoeia in Korea), health functional food standards codex (e.g., "Health Function Food Standards and Specifications" notified by the Korean Ministry of Food and Drug Safety in Korea), compounds or extracts approved according to instructions of each country which regulate production and sales of drug products ("the Pharmaceutical Affairs Act" in Korea), and compounds or extracts which are approved for functionality according to instructions in each country which regulate production and sales of health functional foods (e.g., "the Health Functional Foods Act" in Korea). For example, maca gelatinized powder, creatine, Hovenia dulcis pedicle extract powder, and a vegetable worm fermentation extract; a fermented amino acid complex, Hovenia dulcis pedicle extract powder, and a Rhodiola sachalinensis extract; and L-arabinose, a nopal extract, cinnamon extract powder, a guava leaf extract, digestion-resistant maltodextrin, lyophilized silkworm powder, a Dioscorea batatas alcohol extract, a banana leaf extract, and a mulberry leaf extract, which are recognized as having respective functions of "exercise performance improvement", "fatigue alleviation", and "blood sugar control", according to the Health Functional Foods Act in Korea, may fall within the scope of such compounds or extracts.

At least one of such compounds or natural extracts may be contained in combination with the effective ingredient in the composition of the present invention.

According to a concrete embodiment, the composition of the present disclosure may be regarded as a food.

The food composition of the present disclosure may be prepared into any form, for example, beverages such as tea, juice, a carbonated beverage, an ion beverage, etc.; processed milk products, such as milk, yogurt, etc.; foods, such as gum, rice cake, traditional Korean sweets and cookies, breads, confectionery, noodles, etc.; and agents for health functional foods, such as tablets, capsules, pills, granules, liquids, powders, flakes, pastes, syrups, gels, jellies, bars, etc. In addition, the food composition of the present invention may be in the form of any product complying with legal and functional classifications according to an enforcement at the time of production and distribution. For example, the composition may be a health functional food according to "the Health Functional Foods Act" of Korea or may be confectionery, beans, teas, beverages, or special purpose foods according to the food types stipulated by the Korean Food Standards Codex ("Health Function Food Standards and Specifications" notified by the Korean Ministry of Food and Drug Safety in Korea) of the Food Sanitation Act in Korea.

The food composition of the present disclosure may include a food additive in addition to the effective ingredient. A food additive may be understood as a substance that can be added to, mixed with, or precipitated in a food during food preparation, processing, or preservation. A food additive should be guaranteed safety because it may be ingested together with food every day and for a long period of time. Safety-guaranteed, food additives are limitedly stipulated in terms of components or functions by a food additives codex according to an act in each country ("Food Sanitation Act" in Korea) which regulates the production and distribution of foods. The Korean Food Additives Codex ("Food Additive Standards and Specifications" published by the Korean ministry of Food and Drug Safety) stipulates food additives in terms of components into categories of chemical synthetic products, natural additives, and mixed agents. Such food additives may be divided into sweeteners, flavoring agents, preservatives, emulsifiers, acidifiers, thickeners, etc. in view of functions.

A sweetener, which is to provide a food with a sweet taste, may be used in the food composition of the present invention irrespective of whether natural or synthetic. Preferable is a natural sweetener. Examples of the natural sweetener include sugar sweeteners, such as a corn syrup solid, honey, sucrose, fructose, lactose, maltose, etc.

A flavoring agent, which is to make a taste or a smell better, may be used irrespective of whether natural or synthetic. Preferable is a natural flavoring agent. A natural flavoring agent may be used for nutrition as well as enhancing flavor. Natural flavoring agents may be obtained from apples, lemons, tangerine, grapes, strawberries, peaches, etc. or from green tea leaves, Solomon's seals, bamboo leaves, cinnamon, chrysanthemum, jasmine, etc. In addition, a natural flavoring agent obtained from ginseng (red ginseng), bamboo sprouts, aloe vera, ginkgo nuts, etc. may be used. The natural flavoring agent may be a concentrated liquid or an extract of a solid phase. According to circumstances, a synthetic flavoring agent, such as ester, alcohol, aldehyde, terpene, etc. may be used.

An available preservative may be exemplified by calcium sorbate, sodium sorbate, potassium sorbate, calcium benzoate, sodium benzoate, potassium benzoate, and EDTA (ethylenediaminetetraacetic acid). As an emulsifier, acacia gum, carboxymethylcellulose, xanthan gum, pectin, etc. may be used. Examples of acidifiers include citric acid, malic acid, fumaric acid, adipic acid, phosphoric acid, gluconic acid, tartaric acid, ascorbic acid, acetic acid. An acidifier may be added to adjust a pH of the food composition with the aim of restraining microbial growth as well as improving a taste. Available for use as a thickener are a suspending agent, a precipitating agent, a gelling agent, and a swelling agent.

In addition to the above-mentioned food additives, the food composition of the present disclosure may further comprise bioactive substances or minerals which are known in the art and guaranteed safety as food additives in order to supplement functionality and nutrition.

Such bioactive substances include catechins such as those contained in green tea; vitamins such as vitamin B1, vitamin C, vitamin E, vitamin B12, etc.; tocopherol; dibenzoyl thiamine, etc. Examples of available minerals include calcium agents such as calcium citrate; magnesium agents such as magnesium stearate; iron agents such as iron citrate; chrome chloride; potassium iodide; selenium; germanium; vanadium; and zinc.

The food composition of the present disclosure may contain the above-mentioned food additives in respective appropriate amounts enough to achieve the purposes of addition according to types of the product.

With regard to other food additives available for the food composition of the present disclosure, reference may be made to a food codex or food additive codex according to instruction of each country.

In another embodiment, the composition of the present disclosure may be understood as a pharmaceutical composition.

The pharmaceutical composition of the present disclosure may comprise a pharmaceutically acceptable carrier in addition to the effective ingredient and may be prepared into an oral or parenteral formulation according to administration routes in a typical manner. Here, the term "pharmaceutically acceptable" means retaining no more toxicity than is too high for an application (treatment) subject to adapt without limiting the activity of the effective ingredient.

For oral formulations, the pharmaceutical composition of the present disclosure may be prepared, together with a suitable carrier, into a dosage form, such as a powder, a granule, a tablet, a pill, a sugar-coated pill, a capsule, a liquid, a gel, a syrup, a suspension, a wafer, etc., according to a method known in the art. In this context, examples of pharmaceutically acceptable carriers include: sugars, such as lactose, glucose, sucrose, dextrose, sorbitol, mannitol, xylitol; starches, such as corn starch, potato starch, wheat starch, etc.; celluloses such as cellulose, methyl cellulose, ethyl cellulose, sodium carboxymethyl cellulose, hydroxypropylmethyl cellulose, etc.; polyvinyl pyrrolidone; water; methylhydroxy benzoate; propylhydroxy benzoate; magnesium stearate; mineral oil; malt; gelatin; talc; polyol; and vegetable oil. If necessary, the composition may be formulated, together with a diluent and/or an excipient, such as a filler, a thickener, a binder, a humectant, a disintegrant, etc.

For parenteral formulations, the pharmaceutical composition of the present disclosure may be prepared, together with a suitable carrier, into a dosage form, such as an eye drop, an injection, a transdermal agent, a nasal inhaler, a suppository, etc. A carrier suitable for use in an eye drop may be exemplified by an isotonic solution such as sterile water, a saline, and 5% dextrose. Optionally, benzalkonium chloride, methyl paraben, ethyl paraben, etc. may be used for preservation. When prepared into an injection, the composition may include a carrier such as sterile water, ethanol, polyol, e.g., glycerol or propylene glycol, or a combination thereof. Preferably, a Ringer's solution, triethanol amine-containing phosphate buffered saline (PBS) or sterile water for injection, an isotonic solution such as 5% dextrose, etc. may be used. A transdermal agent may be in the form of an ointment, a cream, a lotion, a gel, an external use liquid, a paste, a liniment, an aerosol, etc. A nasal inhaler may be prepared into an aerosol spray in which a suitable propellant such as dichlorofluoromethane, trichlorofluoromethane, dichlorotetrafluoroethane, carbon dioxide, etc. may be used. For a suppository, Witepsol, Tween 61, polyethylene glycols, cacao butter, laurin butter, polyoxyethylene sorbitan fatty acid esters, polyoxyethylene stearates, sorbitan fatty acid esters, etc. may be used as a base.

Concrete formulations of pharmaceutical compositions are known in the art. For example, reference may be made to document [Remington's Pharmaceutical Sciences (19th Ed., 1995)], which is incorporated herein by reference.

The preferable dose of the pharmaceutical composition in accordance with the present disclosure may vary, depending on various factors including the patient's health state, weight, sex, and age, the severity of disease, and the route of administration. For a preferred effect, the effective amount of the pharmaceutical composition of the present invention may range in a daily dose from 0.001 mg/kg to 10 g/kg, and more preferably from 0.001 mg/kg to 1 g/kg. The composition may be administered in a single dose, or may be divided into multiple doses per day. Such doses should be construed to limit the scope of the present disclosure in no way.

A better understanding of the present invention may be obtained through the following examples which are set forth to illustrate, but are not to be construed as the limit of the present invention.

EXAMPLE

Isolation and Identification of HdP from *Ishige okamurae* Extract

Example 1: Isolation of HdP

Hdp was isolated from an *Ishige okamurae* extract as follows, and a schematic view of the isolation process thereof is depicted in FIG. 1.

*Ishige okamurae* was gathered in an area of Sungsan, Jeju Island, Korea, desalted by washing with fresh water twice, and naturally dried. The dried *Ishige okamurae* was ground into powder in a blender and 100 g of the powder was immersed in 2 L of 50% ethanol for 24 hours at room temperature. Following filtration, concentration at a reduced pressure removed the solvent to leave an extract in a powder phase.

In 5 L of distilled water was suspended 10 g of the extract powder to which 5 L of ethyl acetate was then added to give fractions. Removal of the solvent by concentration at room temperature afforded an ethyl acetate fraction.

For use in centrifugal partition chromatography (CPC), a solvent system consisting of n-hexane-ethylacetate-methanol-water was preferentially selected through a preparative experiment. Investigation was made into an optimal partition coefficient K while component ratios in the solvent system were changed. As a result, a K value of 0.5 was identified to be optimal when n-hexane, ethylacetate, methanol, and water in the solvent system were present at a volume ratio of 1:9:4.5:6.5.

The solvent system was put in a separatory funnel and thoroughly equilibrated by being vigorously shaken at room temperature to separate an upper organic layer and a lower phase which were used as a stationary phase and a mobile phase, respectively.

In order to perform CPC, the CPC column was filled with the upper organic phase (stationary phase). While the column was then rotated at 1,000 rpm, the lower phase was injected at a flow rate of 2 ml/min to the column until the pump pressure was constantly maintained. After the pressure reached a constant value, 60 ml of a sample (a solution of 500 mg of the ethylacetate fraction in 6 mL of a mixture of 1:1 of water and methanol) was injected. While the effluent was monitored at 230 nm, fractions were collected. Relatively non-polar fractions were separated at 70 min to 120 min after the sample injection.

Figure 2:
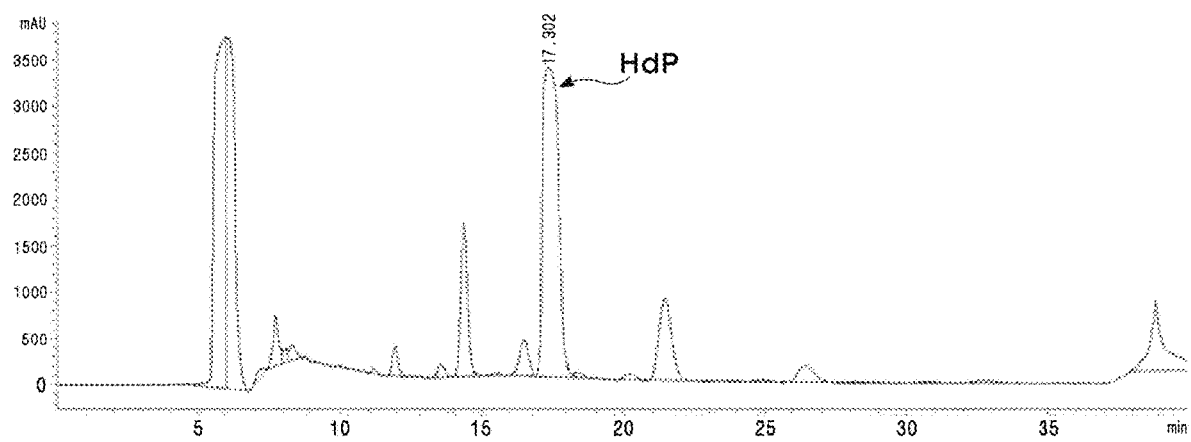
FIG. 2 is an HPLC chromatogram of HdP.

Then, the CPC fractions thus obtained were subjected to HPLC, using a semi-preparative HPLC column (YMC-Pack ODS-A, 10×250 mm, 5 µm particle size, YMC Co Ltd, Tokyo, Japan). In brief, 32% acetonitrile containing 0.1% formic acid and 68% water containing 0.1% formic acid were used as a mobile phase which was allowed to flow at a flow rate of 2 mL/min. The effluent was monitored with a UV detector at 230 nm and a compound having the second highest intensity, detected at 17.302 min, was isolated. An HPLC chromatogram accounting for the compound is depicted in FIG. 2.

Example 2: Identification of the Compound

Figure 4A:
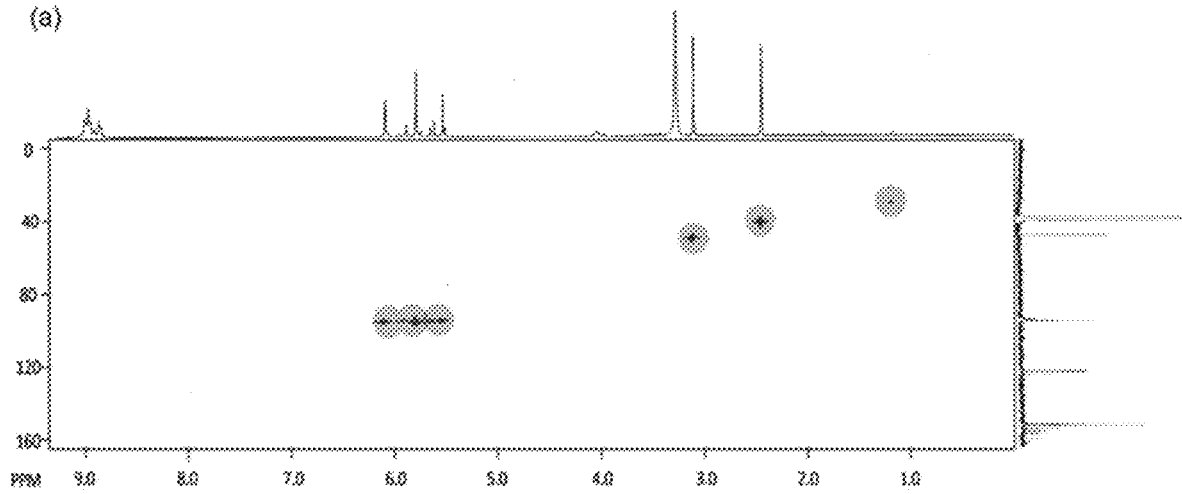
FIGS. 4a and 4b shows two-dimensional NMR spectral HMQC (a) and HMBC (b) data of HdP.
Figure 4B:
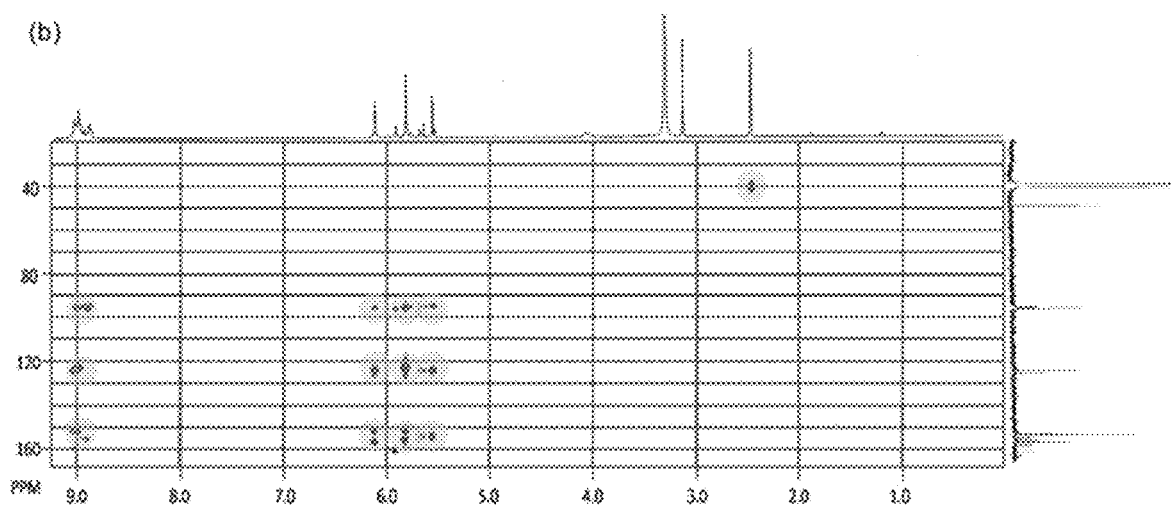
Figure 5:
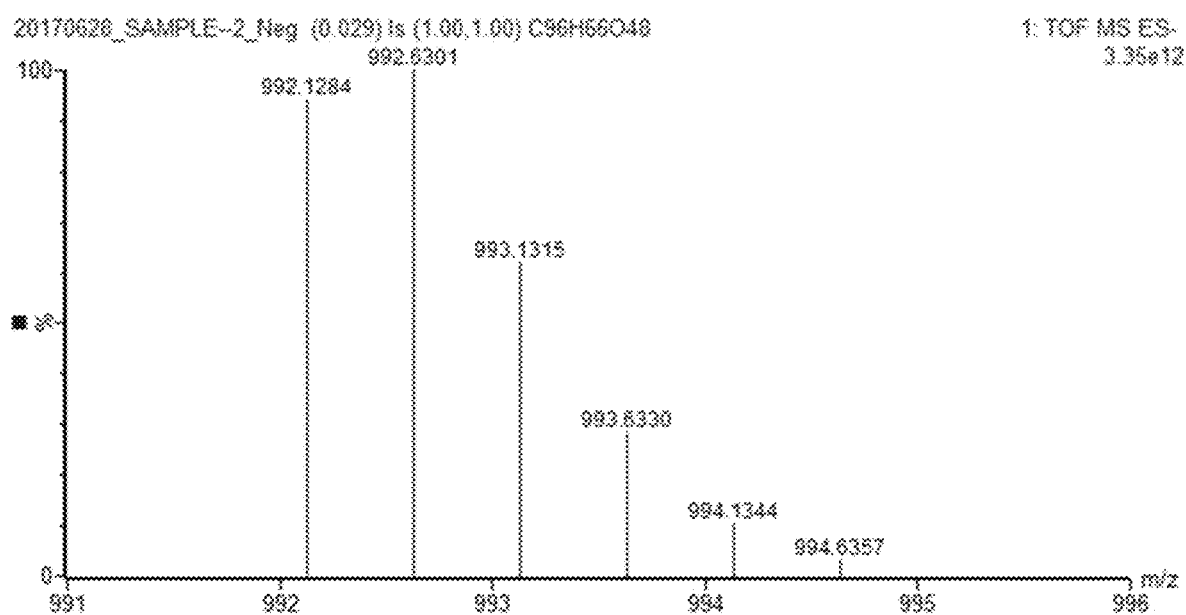
FIG. 5 is an LC-MS-MS spectral data of HdP.

For structural identification of the isolated compound, 1H NMR, and 13C NMR spectra were measured. HMQC and HMBC spectra, which are two-dimensional (2D) NMR spectra, were measured to analyze correlation between hydrogen atoms themselves and between hydrogen and carbon atoms. The molecular weight was determined using LC-MS-MS. The results are shown in FIGS. 3 to 5, respectively. Comparison of the data with those in related documents concluded the identification of HdP, a novel compound represented by Chemical Formula 1.

Experiment Examples: Assay of HdP for Anti-Diabetic Activity and Exercise Performance Improvement Experiment Example 1: Anti-Diabetic Activity of HdP 1.1 Assay of Inhibitory Activity Against α-Glucosidase Inhibitory activity against α-glucosidase was evaluated using a yeast enzyme according to the method of Watanabe et al. (Watanabe, Kawabata, Kurihara, & Niki, 1997). In the reaction condition of pH 7.0 and 37° C., 5 mM p-nitrophenyl α-D-glucopyranoside (PNP-G) serving as a substrate was reacted with a dilution of 32 mU/ml enzyme (yeast α-glucosidase, Sigma) in 100 mM phosphate buffer and inhibitory activity was measured using spectrophotometry. The sample was reacted with PNP-G for 5 min and the absorbance of 4-nitrophenol released upon the hydrolysis of PNP-G was read at 405 nm. Subsequently, the same amount of the substrate solution was added and reacted at room temperature for an additional five min., after which the reaction was stopped by adding 0.5 M $Na_2CO_3$. A change in absorbance at 405 nm was measured.

Inhibitory activity (%) against α-glucosidase was calculated according to the formula (1-absorbance of sample-added group/absorbance of solvent-added group)×100).

Acabose, which is an oral hypoglycemic agent inhibitory of α-glucosidase, was used as a positive control.

1.2 Measurement of Glucose Uptake of C2C12 Cell 1.2.1 C2C12 Cell Culture and Differentiation The mouse-derived myoblast C2C12 cells (ATCC, Manassas, Va., USA) were suspended in DMEM (Dulbecco's Modified Eagle's Media) medium supplemented with 10% FBS and an antibiotic and cultured at 37° C. under a 5% $CO_2$ atmosphere in an incubator. Upon 80% confluency, the C2C12 cells subjected to differentiation in a DMEM medium containing 2% horse serum and a low concentration of glucose for 5 days, with the medium freshly changed every three days. The differentiated cells were serum starved for 12 hours in serum free DMEM containing a low concentration of glucose, washed with PBS, and then reacted for 24 hours with the sample (HdP) in a fresh serum free DMEM.

1.2.2 Measurement of Glucose Uptake of C2C12 Cell Using Flow Cytometry (FACS)

Glucose uptake of mouse-derived myoblast C2C12 cells was measured using flow cytometry (FACS) according to the (2-(N-(7-nitrobenz-2oxa-1,3-diazol-4-yl)amino)-2-deoxyglucose (2-NBDG) assay method (Cell Death Dis. 2017 Oct. 5. 8 (10):e3078). The cultured cells were incubated with 10 µM 2-NBDG at 37° C. for 24 hours and then analyzed using BD FACS Cantoll (BD Biosciences, NJ, USA), with the fluorescence of 2-NBDG detected in a FITC channel.

1.3 Animal Test

For use in experiments, adult zebrafish were purchased from a market (Jeju Aquarium, Jeju Island, Korea). They were acclimated to a condition of a temperature of 28.5±1° C. and a 14/10 h light-dark cycle in a 3.5 L acryl tank and fed twice a day (Tetra GmgH D-49304 Melle, made in Germany). Experiments with zebrafish were approved by the Institutional Animal Care and Use Committee of Jeju University.

1.3.1 Test of HdP Toxicity in Zebrafish Embryo

Four days after fertilization, each of the embryos (n=15) was transferred to 12-well plates, each containing 950 µl of an embryo medium (distilled water containing 60 ppm salt) and 50 µl of HdP (0.01, 0.1, 1, and 10 µg/ml) and the viability of zebrafish embryos exposed to HdP for 168 hours after fertilization were measured.

1.3.2 Measurement of Blood Sugar Level in Zebrafish

Wild-type adult zebrafish were treated for 1 hour with 2 mg/ml alloxan and then for 1 hour with 1% glucose in the absence of insulin. Subsequently, the reaction solution was exchanged with water in which the zebrafish were then left for 1 hour before treatment with HdP, metformin, or BAPTA-AM for 90 min. Thus, the experiment groups included a non-treated group, an alloxan-treated group (control), a group treated with alloxan and HdP (0.3 µg/g body weight), a group treated with alloxan and metformin (5 µg/g body weight), a group treated with alloxan and BAPTA-AM (3 µg/g body weight), and a group treated with alloxan, BAPTA-AM (3 µg/g body weight), and HdP (0.3 µg/g body weight).

2. Test Results 2.1 Measurement Result of Inhibitory Activity Against α-Glucosidase Concentrations of the samples which were necessary for inhibiting the activity of α-glucosidase by 50% ($IC_{50}$) are given in Table 1, below.

TABLE 1

| Sample | $IC_{50}$ (µM) |
| --- | --- |
| Hexadecaphlorethol(HdP) | 54.97 |
| Acarbose | 1050.23 |

As is understood from the data of Table 1, HdP according to the present disclosure exhibited higher inhibitory activity against α-glucosidase than acarbose did.

2.2 Measurement Result of Glucose Uptake of C2C12 Cell

Figure 6:
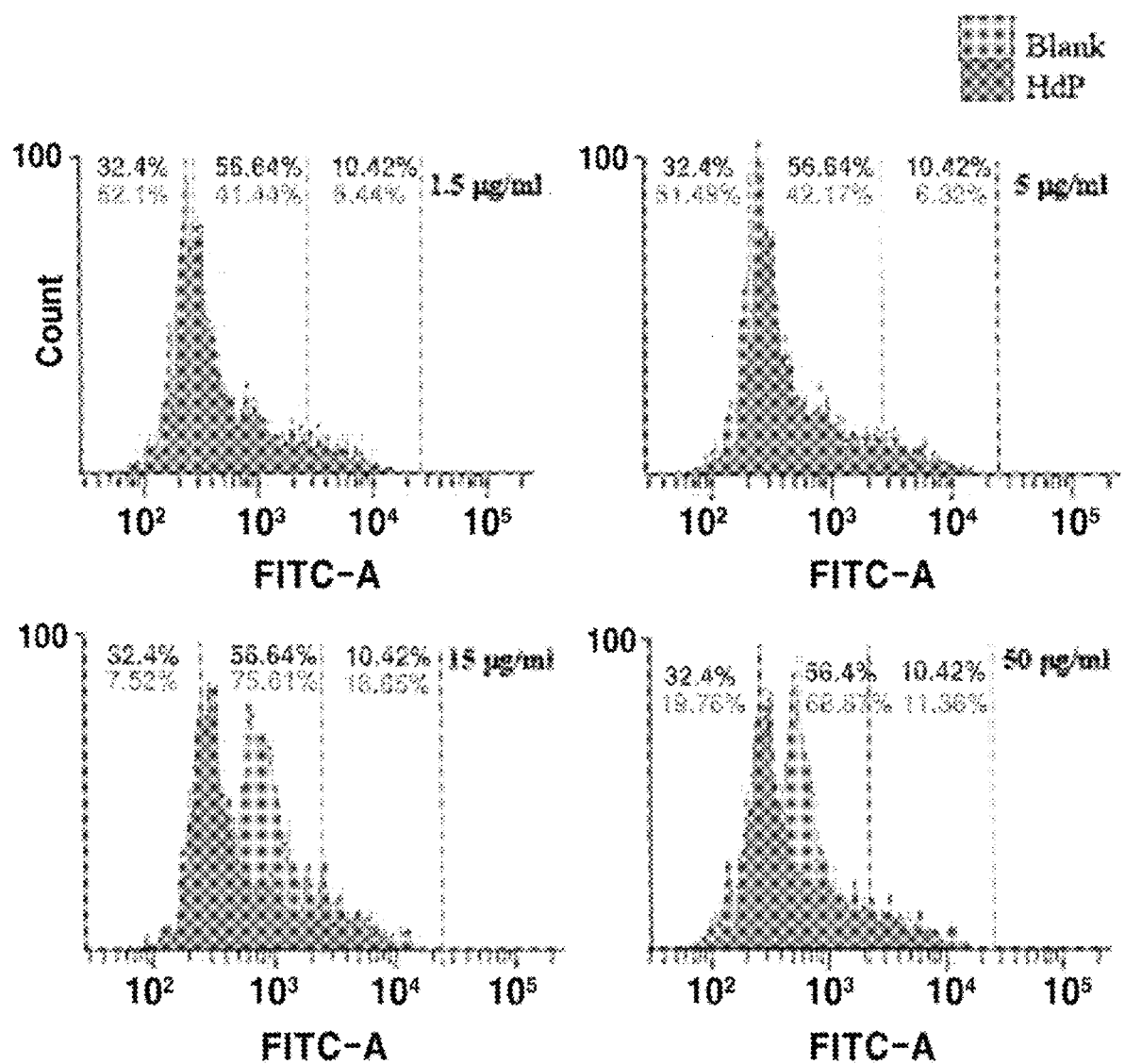
FIG. 6 shows results indicating that HdP induces glucose uptake into differentiated myoblast C2C12 cells.
Figure 7:
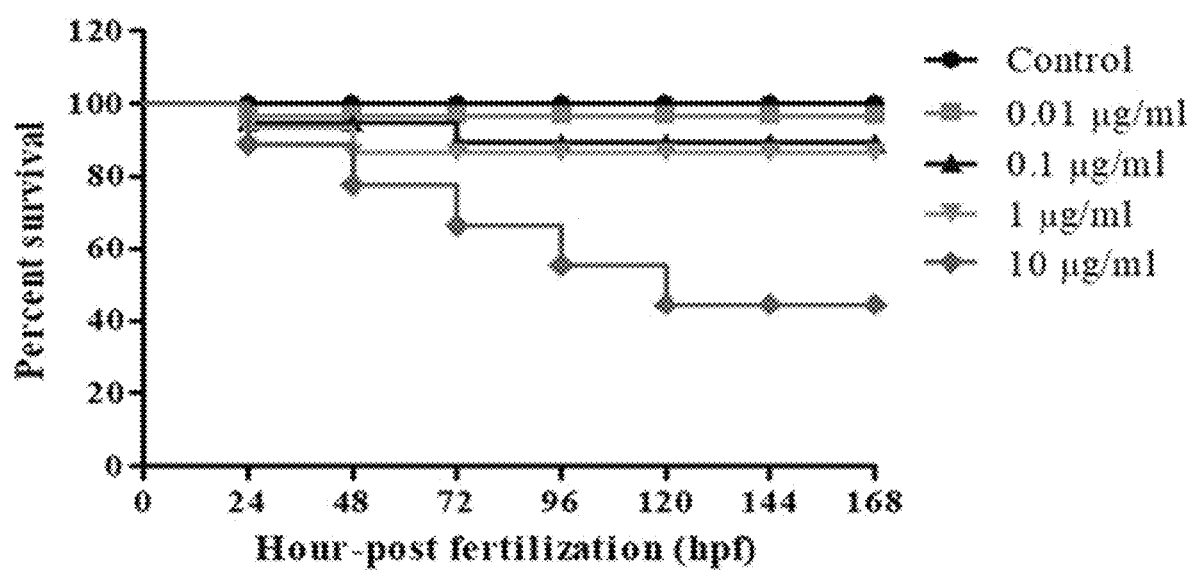
FIG. 7 shows toxicity test results of HdP in zebrafish embryos.

Glucose uptake by HdP in differentiated C2C12 cells was measured and the results are depicted in FIG. 7. FACS is an instrument isolating fluorescence-marked cells from a heterogeneous cell mixture. In C2C12 cells which were treated with the fluorescence-marked glucose analogue 2-NBDG, fluorescence intensity became stronger with the detection of more 2-NBDG through a FITC filter. Thus, the detected cell populations migrated right in the graph. With reference to FIG. 6, glucose uptake into the differentiated C2C12 cells treated with HdP for 24 hours is shown to significantly increase in a dependent manner on the dose of HdP, indicating that HdP can lower a blood glucose level. Glucose uptake into differentiated C2C12 cells is known as an index accounting for a reduction in blood glucose level (Diabetes 30 (1981) 1000-1007; Biochemical and Biophysical Research Communications 420 (2012) 576-581; Nat. Rev. Mol. Cell Biol. 7 (2006) 85-96; Eur. J. Cell Biol. 87 (2008) 337-351)

2.3 Test Result of HdP Toxicity in Zebrafish Embryo

In order to examine a toxicity-free concentration of HdP at which no toxicity occurs, survival rates of zebrafish embryos were evaluated. As shown in FIG. 7, the embryos were observed to survive 1 µg/ml or less HdP at a rate of about 90% or higher.

2.4 Measurement Result of Blood Glucose Level of Zebrafish under Control of HdP

Examination was made to see whether HdP controls blood sugar in an animal model. In this regard, adult zebrafish which had been treated with alloxan to release a reduced level of insulin were injected with glucose and monitored for blood glucose levels.

Figure 8:
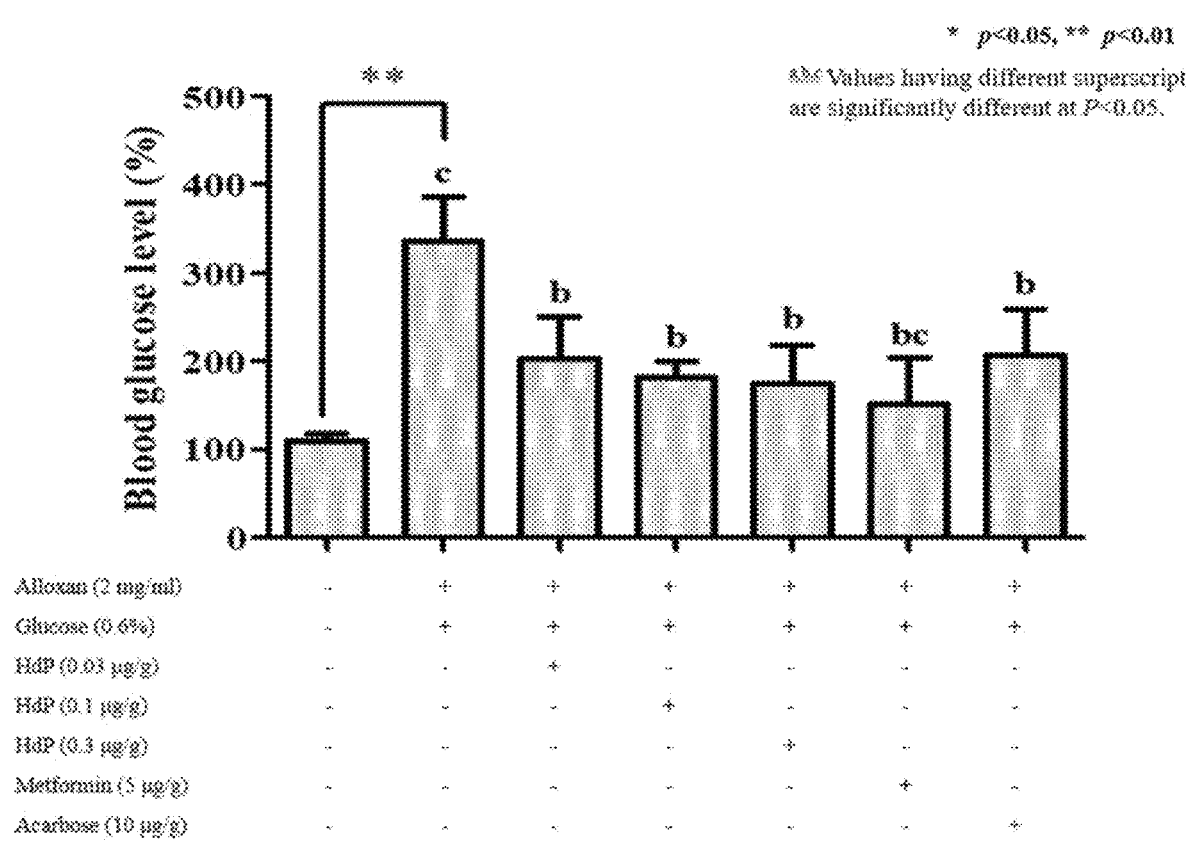
FIG. 8 shows a result illustrating that HdP reduces a blood glucose level in adult zebrafishes.

Results are depicted in FIG. 8. With reference to FIG. 8, HdP was observed to significantly reduce blood glucose levels of alloxan-treated adult zebrafishes in a dose-dependent manner. This effect was similar to that of metformin, which is commercially used to control blood glucose. Particularly, when account is taken of the fact that HdP was used at a concentration of 0.3 µg/g in contrast to 5 µg/g metformin, a similar glucose uptake effect is expected even with a concentration of HdP which is 16.7-fold lower than that of metformin.

Experiment Example 2: Activity of HdP to Improve Exercise Performance

1. Experiment Method 1.1 Preparation of Zebrafish

For use in experiments, adult zebrafish were purchased from a market (Jeju Aquarium, Jeju Island, Korea). They were acclimated to a condition of a temperature of 28.5±1° C. and a 14/10 h light-dark cycle in a 3.5 L acryl tank and fed twice a day (Tetra GmgH D-49304 Melle, made in Germany). Experiments with zebrafish were approved by the Institutional Animal Care and Use Committee of Jeju University.

1.2 Measurement of Intracellular Calcium Level in Zebrafish Embryo Using Fluo-4

Intracellular calcium levels of zebrafish embryos were measured using a calcium-sensitive Fluo-4 probe. Embryos were incubated with Fluo-4 at 28.5±1° C. for 30 min before treatment with HdP (0.6, 3, and 6 µg/ml). In order to block the entry of calcium into cells, the embryos were reacted with the calcium chelator BAPTA-AM 0.1 mM for 1 hour before incubation with Fluo-4. The experiment groups included a non-treated group (N), a group treated with Fluo-4 alone (F), a group treated with HdP alone (0.6, 3, and 6 µg/ml), a group treated with Fluo-4 and HdP (0.6, 3, and 6 µg/ml), and a group treated with Fluo-4, BAPTA-AM, and HdP (6 µg/ml).

1.3 Measurement of Blood Glucose Level of Zebrafish

Wild-type adult zebrafish were treated for 1 hour with 2 mg/ml alloxan and then for 1 hour with 1% glucose in the absence of insulin. Subsequently, the reaction solution was exchanged with water in which the zebrafish were then left for 1 hour before treatment with HdP, metformin, or BAPTA-AM for 90 min. Thus, the experiment groups included a non-treated group, an alloxan-treated group (control), a group treated with alloxan and HdP (0.3 µg/g body weight), a group treated with alloxan and metformin (5 µg/g body weight), a group treated with alloxan and BAPTA-AM (3 µg/g body weight), and a group treated with alloxan, BAPTA-AM (3 µg/g body weight), and HdP (0.3 µg/g body weight).

2. Test Result 2.1 Measurement Result of Intracellular Calcium Level Change by HdP in Zebrafish Intracellular calcium level changes by HdP in zebrafish embryo cells were observed with Fluo-4. Referring to FIG. 9, a significant difference appeared around the abdomen between the non-treated group (N) and the Fluo-4-treated group (F). The group treated with HdP alone did not undergo a special phosphorescence change, compared to the non-treated group (N) or the Fluo-4-treated group (F) (left panel in FIG. 9), indicating no HdP-induced phosphorescence change. A significant increase in phosphorescence was observed in the group treated with HdP and Fluo-4 in combination, compared to the Fluo-4-treated group (F), indicating that treatment with HdP increases intracellular $Ca^{2+}$ levels. A phosphorescence decrease in the group treated with the calcium chelator BAPTA-AM in combination with HdP identified the intracellular influx of $Ca^{2+}$ (right panel in FIG. 9).

2.2 Measurement Result of Blood Glucose Level Change by HdP in Zebrafish

Figure 10:
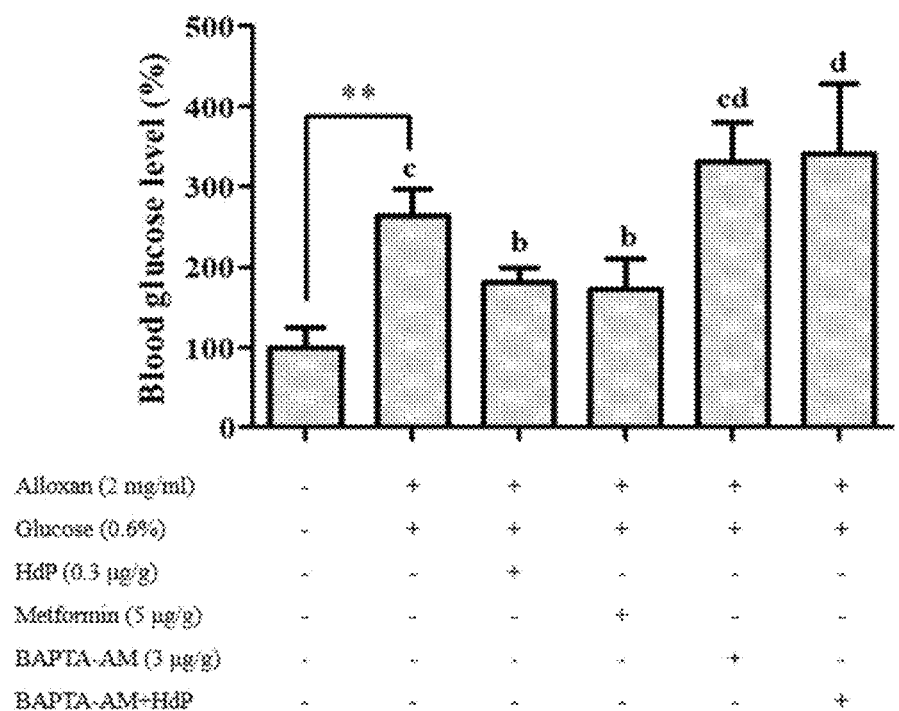
FIG. 10 shows a result illustrating that HdP induces glucose influx into zebrafish myocytes.

Examination was made to see whether HdP induces the uptake of glucose necessary for muscle contraction with the increase of intracellular $Ca^{2+}$ levels. In this regard, adult zebrafish which had reduced insulin secretion by treatment with alloxan were injected with glucose to monitor HdP-induce glucose influx into myocytes in terms of blood glucose levels. The results are shown in FIG. 10. A reduced level of the energy source glucose in blood is known as an index accounting for glucose influx into tissues, such as muscles, etc. (Diabetes 30 (1981) 1000-1007; Biochemical and Biophysical Research Communications 420 (2012) 576-581; Nat. Rev. Mol. Cell Biol. 7 (2006) 85-96; Eur. J. Cell Biol. 87 (2008) 337-351).

Blood glucose levels in the alloxan-treated adult zebrafishes were significantly reduced by HdP. This effect was similar to that of metformin, which is commercially used to control blood glucose. Particularly, when account is taken of the fact that HdP was used at a concentration of 0.3 μg/g in contrast to 5 μg/g metformin, a similar glucose uptake effect is expected even with a concentration of HdP which is 16.7-fold lower than that of metformin.

A relation between an effect of HdP on glucose influx and an increase of intracellular calcium levels was investigated. For this, zebrafish were treated with the calcium chelator BAPTA-AM in combination with alloxan or HdP. No significant differences in blood glucose level were observed between the groups treated with alloxan plus BAPTA-AM and with HdP plus BAPTA-AM, indicating that glucose uptake in adult zebrafish increases with the HdP-induced increase of intracellular calcium levels.

Provided according to the present disclosure is a composition for improving exercise performance, using a novel compound HdP isolated from *Ishige okamurae*, as described hitherto. The composition of the present invention may be prepared into a food or drug product.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating diabetes, comprising:
administering to a patient in need thereof a therapeutically effective amount of a compound of Chemical Formula 1, a hydrate thereof, or a solvate thereof:

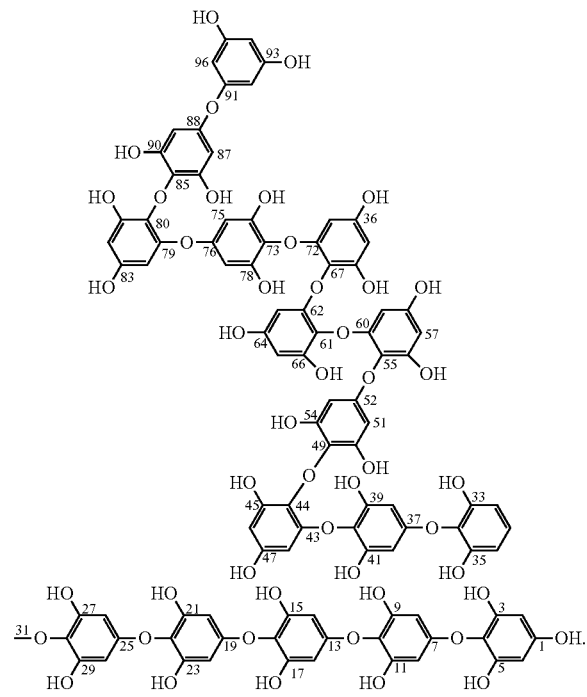

Chemical Formula 1

2. The method of claim 1, wherein the compound is administered in a form of a pharmaceutical composition.

3. The method of claim 2, wherein the composition comprises at least one excipient.

4. The method of claim 2, wherein the pharmaceutical composition further comprises at least one selected from the group consisting of maca gelatinized powder, creatine, Hovenia dulcis pedicle extract powder, and a vegetable worm fermentation extract; a fermented amino acid complex, Hovenia dulcis pedicle extract powder, and a Rhodiola sachalinensis extract; and L-arabinose, a nopal extract, cinnamon extract powder, a guava leaf extract, digestion-resistant maltodextrin, lyophilized silkworm powder, a Dioscorea batatas alcohol extract, a banana leaf extract, and a mulberry leaf extract.

5. The method of claim 1, the compound is administered in a form of a food composition.

6. The method of claim 5, wherein the food composition is in a form selected from the group consisting of tea, juice, carbonated beverage, ion beverage milk, yogurt, gum, rice cake, traditional Korean cookies, breads, confectionery, noodles, granules, liquids, powders, flakes, pastes, syrups, gels, jellies, and bars.

7. The method of claim 5, wherein the food composition further comprises at least one selected from the group consisting of sweeteners, flavoring agents, preservatives, emulsifiers, acidifiers, and thickeners.

8. The method of claim 5, wherein the food composition further comprises at least one selected from the group consisting of maca gelatinized powder, creatine, Hovenia dulcis pedicle extract powder, a vegetable worm fermentation extract; a fermented amino acid complex, Hovenia dulcis pedicle extract powder, a Rhodiola sachalinensis extract; L-arabinose, a nopal extract, cinnamon extract powder, a guava leaf extract, digestion-resistant maltodextrin, lyophilized silkworm powder, a Dioscorea batatas alcohol extract, a banana leaf extract, and a mulberry leaf extract.

* * * * *